(12) United States Patent
Dampeirou

(10) Patent No.: US 6,190,664 B1
(45) Date of Patent: Feb. 20, 2001

(54) DEPIGMENTING COSMETIC SKIN-CARE COMPOSITION AND USE THEREOF

(75) Inventor: Christian Dampeirou, Allonne (FR)

(73) Assignee: C 3 D (FR)

(*) Notice: Under 35 U.S.C. 154(b), the term of this patent shall be extended for 0 days.

(21) Appl. No.: 08/981,701

(22) PCT Filed: Jul. 5, 1996

(86) PCT No.: PCT/FR96/01051

§ 371 Date: Feb. 6, 1998

§ 102(e) Date: Feb. 6, 1998

(87) PCT Pub. No.: WO97/02807

PCT Pub. Date: Jan. 30, 1997

(30) Foreign Application Priority Data

Jul. 7, 1995 (FR) .................................. 95 08242

(51) Int. Cl.⁷ ........................... A61K 35/78; A61K 7/021
(52) U.S. Cl. ................... 424/195.1; 424/401; 424/62-63; 424/78.02; 424/78.03; 514/844; 514/937; 514/944; 514/460; 514/557
(58) Field of Search ................................ 424/195.1, 401, 424/62, 63, 78.02, 78.03; 514/460, 844, 937, 944, 557

(56) References Cited

U.S. PATENT DOCUMENTS 5,362,494 * 11/1994 Zysman et al. ..................... 424/401
5,759,524 * 6/1998 Tanner et al. ........................ 424/59

FOREIGN PATENT DOCUMENTS

2259014 * 3/1993 (GB) .
2028105 * 1/1990 (JP) .
6128138 * 5/1994 (JP) .
7061915 * 3/1995 (JP) .

* cited by examiner

*Primary Examiner*—Christopher Tate
(74) *Attorney, Agent, or Firm*—Bierman, Muserlian and Lucas

(57) ABSTRACT

A cosmetic skin-care composition containing as the active principle a depigmentationally active combination of (a) an acidic mixture including (i) at least one α-hydroxylated acid or a derivative thereof, with the exception of ascorbic acid, and (ii) at least one compound selected from the group which consists of kojic acid, caffeic acid, azelaic acid, aminobutyric acid, fusaric acid, 5-hydroxy 2-hydroxymethyl-γ-pyridone, and derivatives thereof, and (b) at least one active component of a plant extract from at least one plant selected from white mulberry, liquorice, skull cap, grapefruit, birch, heather, strawberry tree, bearberry, lemon, lettuce, oarweed, cucumber, ginseng, hop, sweet corn, feverfew, sage, soya, elder, spirulina, lime, ferocious aloe, yukinoshita, bloodwort, hoelen, wood rose, α-orizanol, burnet, ginkgo biloba, tanlex VB and Eclipsa alba, with the proviso that when the composition contains kojic acid and a liquorice extract, it contains at least one other plant extract component. The use of said composition for preparing a drug or in a cosmetic method is also disclosed.

7 Claims, 3 Drawing Sheets

DEPIGMENTING COSMETIC SKIN-CARE COMPOSITION AND USE THEREOF

This invention relates to compositions showing a depigmenting activity and to their uses.

STATE OF THE ART

The brown marks are localized hyperpigmentations which are caused by an excess of melanin.

The skin melanic marks which become more pronounced or which appear with the age, are experienced as an esthetical trouble which is always hard to bear on a psychological level.

Depending on their origin, hyperpigmentations are classified into two main groups:
1) Hyperpigmentation Bound to Melanocytar Hyperactivity and Hyperpigmentation Bound to Melanocytar Proliferation
a) Ephelids Commonly called brown blotches, they appear during childhood, mainly on clear skins and are preferentially located on the uncovered parts of the epidermis. They intensify after expositions to the sun.

Histologically, the number of melanocytes is normal but the amount of melanin is increased.
b) Lentigine or Solar Lentigo They are rounded and flat marks of very small size, having a taint from brown yellow to black, appearing during childhood. It is practically impossible to differentiate them from the ephelids when they are not of very dark colour.
c) Senile Lentigo They are brown marks appearing on the back side of the hands, on the forearms and on the face after the fifties. Histologically it is noted a melanic hyperpigmentation of the basal layer of epidermis with an increase of the number of melanocytes.
d) Melasma It is a pigmental layer extending in a almost always symetrical manner on the forehead and the cheeks, more frequently appearing in the brown ladies. It may appear in three opportunities:

during pregnancy: it is chloasma, during the intake of oestroprogestative agents, in an idiopathic manner.
2) Hyperpigmentation by Pigmentar Incontinence This is a hyperpigmentation consecutive to photosensibilization.

This is the classical dermatosis as a charm or perfume dermitis. They are brown, more or less dark, marks, laid out in packs or in runnings at the location where the perfumes and the cosmetics are applied before a sun exposition. They gradually and spontaneously disappear in several months.

SUMMARY OF THE INVENTION

It hence exists a need for a composition having a high depigmenting activity at low concentration, showing a good skin tolerancy.

Therefore this invention has as a subject matter, dermocosmetic compositions, wherein they contain as an ingredient a combination endowed with depigmenting activity:

a) An Acid Mixture Comprising i) at least an α-hydroxylated acid or one of the derivatives thereof, ii) at least one compound selected from the group consisting of kojic acid, caffeic acid, azelaic acid, aminobutyric acid, fusaric acid, 5-hydroxy 2-hydroxymethyl-γ-pyridone, and the derivatives thereof, (b) at least one active ingredient from a plant extract from at least one plant selected from white mulberry, liquorice, skull cap, grapefruit, birch, heather, strawberry tree, bearberry, lemon, lettuce, oarweed, cucumber, ginseng, hop, sweet corn, fever few, sage, soya, elder, spirulina, lime, ferocious aloe, yukinoshita, bloodwort, hoelen, wood rose, α-orizanol, burnet, Ginkgo biloba, tanlex VB, Eclipsa alba, with the proviso that when the composition contains kojic acid and liquorice, it contains at least another component from a vegetal extract.

Preferably ascorbic acid will be excluded from the usable acids mentioned under a). Among the derivatives of acids i) and ii) it needs to be cited the salts, mainly the alkali or earth alkaline metal salts and particularly the ammonium salts. Among the derivatives it may also cited the esters mainly the esters with the polyols for example the sugars.

It may particularly be contemplated co-esters with two acid derivatives on a same polyol.

Among the usable α-hydroxylated acids, it has to be cited malic and citric acid, lactic acid, and glycolic acid; the concentration thereof is advantageously comprised between 0.1 and 45% in relation to the total weight of the composition.

Acids ii) providing more advantageous results according to the invention, are kojic acid, caffeic acid, or 5-hydroxy 2-hydroxymethyl-γ-pyridone, the last compound being more particularly preferred. It will be then preferably used, these compounds or the salts thereof, alone or in a mixture to constitute the non α-hydroxylated acid moiety of the depigmenting compositions.

Some particularly advantageous combinations are those comprising a mixture of kojic acid, Burnet and Eclipsa alba. The latter may be combined with α-hydroxylated acids and optionally other components of vegetal extracts.

The active ingredient of a vegetal extract may be obtained by extraction from the plant or a part of the plant but it may be possible to obtain this component by chemical synthesis when this has been identified. This synthesis may be complete or be hemisynthesis.

The active ingredient is preferably brought by a vegetal extract obtained from white mulberry, liquorice, scuttellaria, grapefruit, birch, heather, strawberry tree, bearberry, lettuce, soja, Aloe ferox, yukinoshita, rose fruit, burnet and/or Eclipsa alba.

When they are obtained by extraction, the active components of the vegetal extracts may be obtained through a step of extraction in a hydroalcoholic medium from the stems, the leaves and/or the roots of the plants. In most of the cases, the hydroalcoholic extract containing the active ingredient and other components may be used as such, but it is obviously possible to eliminate from this extract the unuseful or noxious components if any and that by known methods such as selective precipitation, extraction by solvent and/or chromatography.

The nature of the active ingredient may very largely vary as a function of the activity of the two moieties, particularly as a function of the activity of the vegetal active component. It is so when the acidic mixture may constitute from 0.1 to 99% by weight of the active ingredient, the vegetal extract constituting thereby the complement.

Preferably the ratio by weight between the acidic moiety and the active component of the vegetal extract is comprised between 50/50 and 70/30.

The compositions according to the present invention may contain other active ingredients disregarding them in the preceding percentages. So, according to one of the aspects of the invention, the composition may further contain at least one compound selected among the ceramides, the vectorizing macromolecules, or component promoting the penetration.

As previously mentioned, the acidic mixture may at least be partially grafted on sucro esters. The concentration into actives in the composition will preferably be comprised between 1 and 20%.

A composition according to the invention shows particularly the following formulation:

Kojic acid: from 1 to 15%

Glycolic acid: from 20 to 30% and from 20 to 35% of the vegetal extracts resulting from Tanlex VB, (extraction solvent is a mixture of water and butylene glycol). Yukinoshita, Naringin, Sohakuhi Bg (extraction solvent is butylene glycol), white mulberry, Lemon Bg, and the remainder in carrier suitable for this formulation.

Finally, melanin protects the skin from the noxious effects of the UV rays. Taking account of the fact that the compositions according to the invention, reduce the production of melanin, it is of interest to add to the cosmetic formulation sun protective agents, very efficient to avoid the damages incurred by the skin exposed to the sun without protection.

These sun protective agents may be organic and/or mineral filters known from the skilled scientists. Among the latters it may be cited the particles of metallic oxide, namely of titanium, iron, cerium, aluminum, etc., and of talc.

The selection of the type of retained filter, its content and optionally its granulometry will be determined by the desired final consistency of the formulation.

The compositions according to the invention may be presented in the form mainly of a lotion, a gel, an emulsion, a cream, an unguent and contain pharmaceutically and/or cosmetologically acceptable suitable carriers. Among these carriers it may be cited the preservatives, the anti-oxydants, the colouring matters, the perfumes, the tensio-active agents, the thickening agents known from the skilled men. They may also contain activity adjuvants and/or another active ingredient.

The following examples are intended to illustrate the invention without in no way restricting its scope.

BRIEF DESCRIPTION OF THE DRAWINGS

In these examples one has to refer to the following figures.

EXAMPLE I

Figure 1:
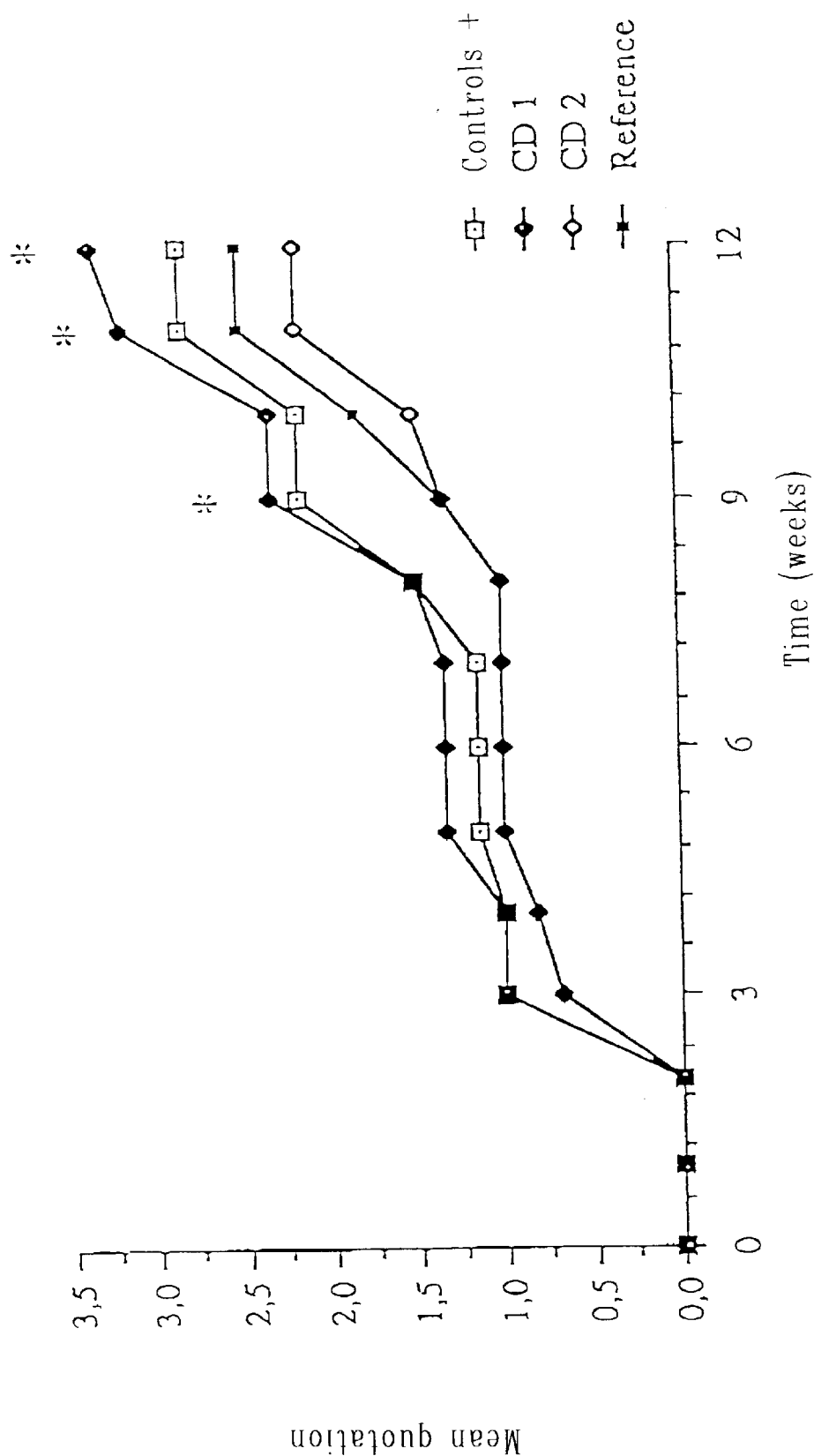
FIG. 1: macroscopical determination of the depigmenting action of various compositions.

Preparation of a Composition According to the Invention

The active ingredient has the following formulation:

| Kojic acid | 10 | |
| --- | --- | --- |
| EDTA | 0.5 | |
| Na sulfite | 0.3 | Acidic moiety (i) 38.5 |
| Na metabisulfite | 0.3 | |
| Glycolic acid | 28.5 | |
| Tanlex VB | 2 | |

-continued

| Yukinoshita | 1 | |
| --- | --- | --- |
| Naringin (extract of grapefruit) | 0.75 | |
| Sohakuhi Bg | 7.5 | Vegetal extracts (ii) 26.75 |
| White mulberry | 13 | |
| Lemon Bg | 2.5 | |
| H$_2$O | 0.5 | |

Operating Technique

In one part of water the preservatives and glycolic acid then kojic acid are dissolved, then heat to 75 C. and slowly add the moiety ii).

The formulation of example I will be designated as Bruni clear in the remaining part of the examples.

EXAMPLE II

In vitro Comparative Study of the Action of Various Compounds on the Tyrosinase Activity Study of the Active Ingredients in the Absence of UV and of Singulet Oxygen 1—Principe of the Method Tyrosinase is able to catalyze the following reactions:

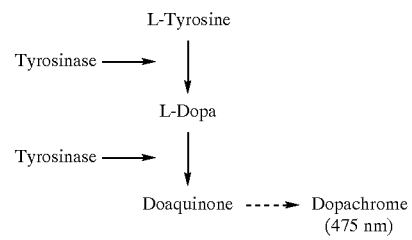

Now one of the hypothesis through which it has to be understood that the invention is not limited, is that the compositions according to the invention behave as a plurifunctionnal inhibitor of tyrosinase, thanks to a synergy between the various constituents. In fact, the two first steps of the synthesis of melanin consist in the action of tyrosinase on Tyrosine, then on L-Dopa or levodopa. The inhibition of the activity of tyrosinase then blocks the formation of melanin.

One of the interests of the composition according to the invention is that it acts as a competitive inhibitor which blocks in a reversible manner the enzymatic reaction, since it does not modify the structure of the enzyme but is only competiting with the natural substrates, tyrosinase or DOPA.

The following test then allows to measure the inhibition of tyrosinase while dosing Dopachrome which is a coloured compound which may spectroscopically be dosed 475 nm.

In order to study the influence of some compounds on the enzymatic activity of tyrosinase, the enzymatic kinetics are achieved.

The reaction is performed at 25° C. in phosphate buffer pH7. Tyrosinase is brought together with its substrate L-Dopa. In the reaction medium it may be added the molecule to be studied.

One compares further the variation in optical density per minute of the test (in the presence of the molecule to be studied) to that of the controls (without molecule). The influence of the molecule on tyrosinase activity will be deduced. The results are then expressed as a percentage of activity knowing that the controls show 100% activity.

| 2 Protocol | | | |
|---|---|---|---|
| | Blank | Controls | Test |
| PBS | 1 ml | 1 ml | 0.8 ml |
| L-Dopa 10-3M | 0.125 ml | 0.125 ml | 0.125 ml |
| Sample | 0.200 ml | / | 0.200 ml |
| Tyrosinase 600 U/ml | / | 0.125 ml | 0.125 ml |

Appearance of Dopachrome at 475 nm is followed for 3 minutes.

Results of the in vitro inhibition of tyrosinase

| Sample | Tested concentration | % of activity | % of inhibition |
|---|---|---|---|
| Controls | | 100 | 0 |
| Santoline | 3.33 mg/ml | 252 | 0 |
| " | 6.66 mg/ml | 299 | 0 |
| Bergamote orange | 3.33 mg/ml | 115 | 0 |
| " | 6.66 mg/ml | 105 | 0 |
| Kojic acid | 10 mg/ml | 20 | 80 |
| " | 1 mg/ml | 29 | 71 |
| Ascorbyl Palmitate | 1 mg/ml | 34 | 66 |
| Hydroquinone | 4 mg/ml | 241.9 | 0 |
| " | 8 mg/ml | 229.41 | 0 |
| " | 16 mg/ml | 112.53 | 0 |
| Reference product M | 50 mg/ml | 36.68 | 63.32 |
| " | 25 mg/ml | 69.94 | 30.06 |
| " | 17 mg/ml | 76.21 | 23.79 |
| Bruni clear ® | 0.10 mg/ml | 36 | 64 |
| " | 0.20 mg/ml | 24 | 76 |
| " | 0.5 mg/ml | 2 | 98 |
| " | 1 mg/ml | 0.6 | 99.4 |
| " | 5 mg/ml | 0 | 100 |
| " | 25 mg/ml | 0 | 100 |
| " | 50 mg/ml | 0 | 100 |

M: Melawhite active ingredient from Pentapharm, composition not disclosed.

M: Melawhite active ingredient from Pentapharm, composition not disclosed.

EXAMPLE III

Formula of a cream Bruni clear at 10%

| | % |
|---|---|
| Active ingredient (according to example I) | 10 |
| Stabilizing antioxydant | 0.25 |
| Gamma orizanol | 0.8 |
| Lecitin | 1 |
| Avocadine | 4 |
| Squalene | 2 |
| Paraffine oil | 4.25 |
| Stearic acid | 2.5 |
| Propylene glycol | 5 |
| Phenonique | 0.25 |
| Norgel | 5 |
| $H_2O$ | QSP |

EXAMPLE IV

Study of the Depigmentating Activity of a Cream Containing Bruni Clear at 10% V. Hydroquinone at 5%

Creams have been prepared according to example III and while substituting in the formula of example III, the active ingredient with respectively hydroquinone at 5% or with kojic acid at 1,5%, only the percentage of water varies.

The study performed by CECMA (Centre d'Etudes et d'Exploitation de Cosmétiques de Médicaments et d'Aliments) had as an objective to appreciate in the pigmented mice, efficiency of two novel depigmenting creams referenced as Bruni clear ® and AK 1.5% in comparison with controls (+) constituted by hydroquinone at 5% and with a reference cream taken up on the market.

From a macroscopical point of view, cream Bruni clear® shown the best depigmenting efficacy before the controls (+), the reference product and cream AK 1.5.

Furthermore on the histological level, the cream Bruni clear® appeared to be as active as the controls (+) and significatively better than Cream AK 1.5% and than the reference product. In view of this results, it may be considered that the cream Bruni clear® is endowed with a depigmenting activity at least equivalent to that of the controls (+) and, in any case, higher than the other formulation tested and than the reference product.

It has to be noted that tolerancy of cream Bruni clear® moreover appeared as good, since no significant cutaneous lesion has been registered after 12 weeks plication. It has also to be noted that the law prohibits the use of hydroquinone at sages higher than 2%.

EXAMPLE V

Study of Depigmenting Activity in the Mice

1—Material and Methods 1.1 Animals

The study has been performed in pigmented male mice of strain $C_3H$ originating from Centre de Recherches et d'Elevage des Oncins IFFA CREDO, B.P. 109, 69592 L'Arbresle Cedex. These animals have not been subjected to any other testing previously and their mean weight was about 20 g at the beginning of the study.

1.2 Conditions for Caging in and Feeding

One week prior to testing, the animal have been placed in cages in polypropylene provided with dust removed, sawdust under standardized housing conditions (temperature of 20±2° C., light 12 hours out 24) and have taken feeding (specific feed for rodents in the form of granulates n° 404 UAR, 7 rue Gallieni 91360 Villemoisson-sur-Orge) and water from public distribution network to satiety.

1.3 Operating Method

Preparation and constitution of the batches of animals:

The animals have been divided randomly in four batches of 6, in the follower manner:

batch 1 or Controls (+): constituted with 6 animals treated with an emulsion °/$_w$ containing 5% hydroquinone, batch 2 constituted with 6 animals treated with product CD 1 (=Bruni clear®), batch 3 constituted with 6 animals treated with product CD 2, i.e. Kojic acid at 1%, batch 2 constituted with 6 animals treated with a reference branded composition directly taken from the market (Depigmenten® batch n° 10405).

A fifth batch constituted with 4 animals treated with a placebo preparation made of vaseline, has been used as controls for normal pigmentation to appreciate the effects of various treatments.

Treatments

The animals have been treated for 6 days per week during 12 consecutive weeks with an application of a suitable amount of the preparations to be tested on the skin of the tail followed by a weak massage intended to insure the penetration of the active ingredients.

Performed Examinations a) Macroscopic Evaluation of the Intensity of the Depigmentation In a regular manner during the study (once per week) and at the end of that the application areas have been observed and the intensity of the pigmentation blindly evaluated using the following numeral evaluation scale:

| Numeral evaluation of intensity of the depigmentation at the macroscopical examination | |
|---|---|
| No depigmentation | 0 |
| Doubtful depigmentation | 1 |
| Presence of small marks very clear, of depigmentation | 2 |
| Medium depigmentation with persistency of areas of normal colouration | 3 |
| Moderately strong depigmentation with uniform loss of the colouration of the skin | 4 |
| Total depigmentation (white skin) | 5 | b) Appreciation of the Local Tolerancy

Parallel to the foregoing examination the condition of the skin at the level of the application areas has been observed to determine the cutaneous tolerancy for the tested products.

c) Histological Examination

At the end of the study after the macroscopical observations, the animals have been sacrificed then or biopsy of the skin has been performed at the level of the application sites. Examination of the histological testings has been performed blindly by an experimenter ignoring the attribution order of the treatments for the animals.

1.4 Expression of the Results and Statistical Analyses

Macroscopic Evaluation

The macroscopic scores determined at each examination have been globally analysed by means of the non-parametric test of Kruskal-Wallis.

Reading of the Histological Results

In the mice which have not received any active treatment, it has been noted at the magnifying×40, the presence of ring-shaped structures lined with hair groupings. It has been numbered between 52 and 106 of these rings per examined slice. For the interpretation of the results, it has been considered that the normal pigmented appearance of such a ring was formed of a build-up of melanocytes in the basal layers of epithelium with a migration of melanic pigments through the horny layer and a moderate pigmentar reuptake in the form of rare melanophages in the underlying dermis.

In order to evaluate the pigmentation it has been carried out:

the posting of the whole number of rings to be studied, the posting of the number of rings showing a normal pigmentation on the basis of the above-mentioned criteria, the posting of the number of rings conversely showing not any pigmentation, the inference on a last time of the hyperpigmentations rings.

The lack of pigmentation has been defined by the complete absence of melanocytes and pigments in a ring or epithelial edge.

Hypopigmentation appeared to be variable but might be characterized by a clear scarcity of the melanocytes in the basal layers, by the lack of migration of the pigments through the horny layers and by a pigmentar uptake sometimes more copious in the underlying dermis.

The way of interpretation has consisted in appreciating for each of the preparations the percentages of edges showing:

1—a normal pigmentation,

2—a partial pigmentation,

3—a non existent pigmentation.

Quotations (c) have further been allocated to the edges as a function of the modifications in the pigmentation using the numerical scale as below:

Numerical evaluation of the pigmentations of the cutaneous edges at the histological examination:

normal pigmentation: 0 partial pigmentation: 1 non existent pigmentation: 2

An index of depigmentation has been calculated for each preparation, corresponding to the sum of quotations divised by the number of observed edges.

$$I_D = \frac{\sum Gi}{N}$$

wherein

G=individual quotation of the rings

N=whole number of the rings

Significativity

The significativity of the various statistical tests has been retained for $p \leq 0.05$.

2—Results 2.1 Macroscopical Observations

The evolution in the course of time of the mean values of each group of animals has been depicted in the FIG. 1. Examination of that shows that the depigmenting action shows itself more or less clearly at the end of 3 weeks, whatever is the treatment. It is then observed the persistancy of a weak even incertain depigmentation during about 6 weeks. It is from this time that the depigmenting effects appear more significative, particularly for cream CD1 and the controls (+) which then differentiate themselves from the two other treatments from a statistical point of view. The effects still intensify themselves between the tenth and the eleventh week (for all the treatments). In the course of the last week of treatment, only cream D1, improved the cutaneous depigmentation.

2.2 Histological Analysis

Figure 2:
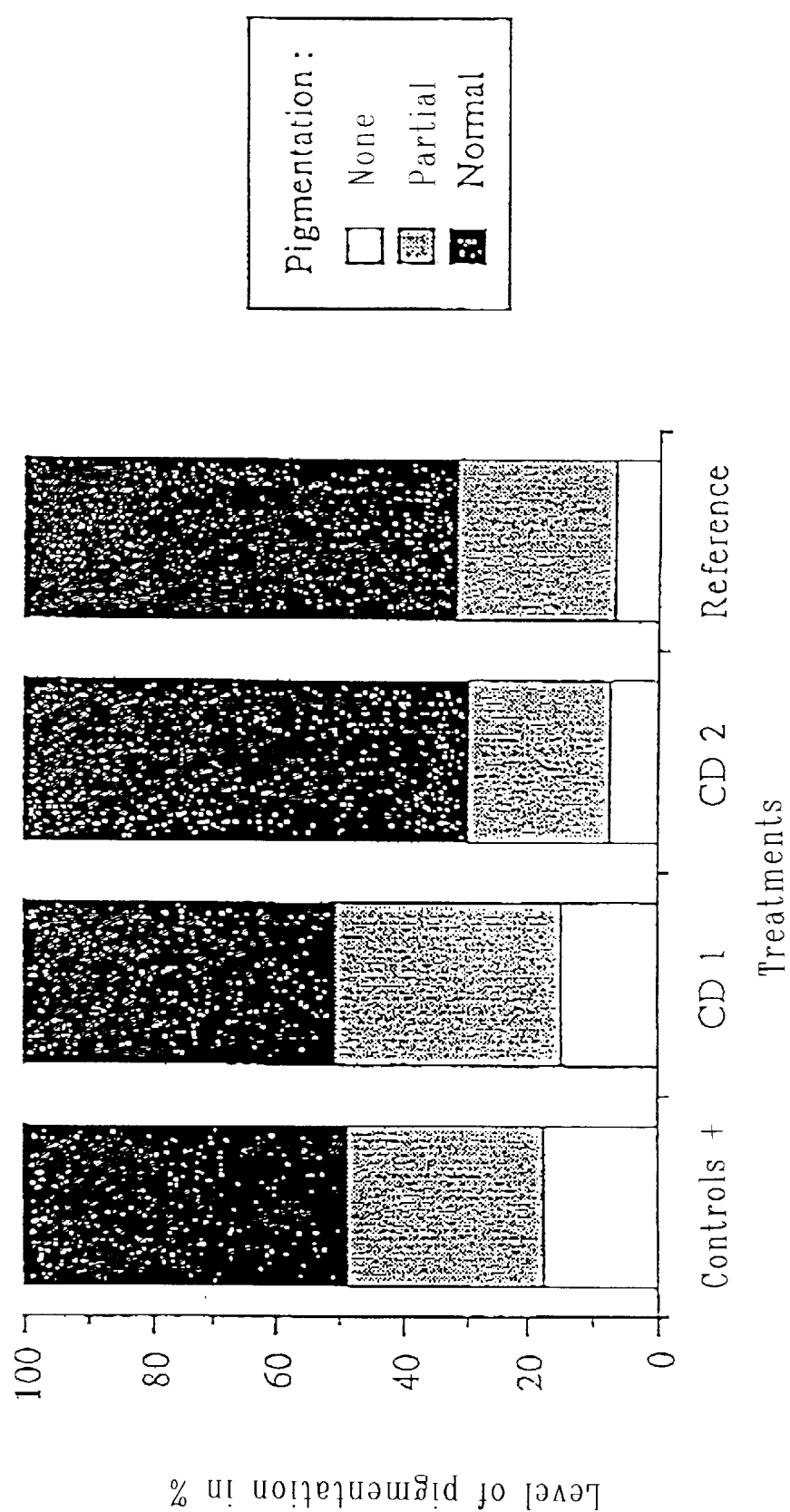
FIG. 2: influence of the treatments on the pigmentar appearance of the application area at the histological examination.

FIG. 2 shows the influence of the treatments on the pigmentar appearance of the application area. It may be stated that the preparations from the controls (+) group and from the group treated with the cream CD1 evidenced a greater number of apigmented or hypopigmented epithelial edges in relation to the preparations of the two other groups of animals.

Figure 3:
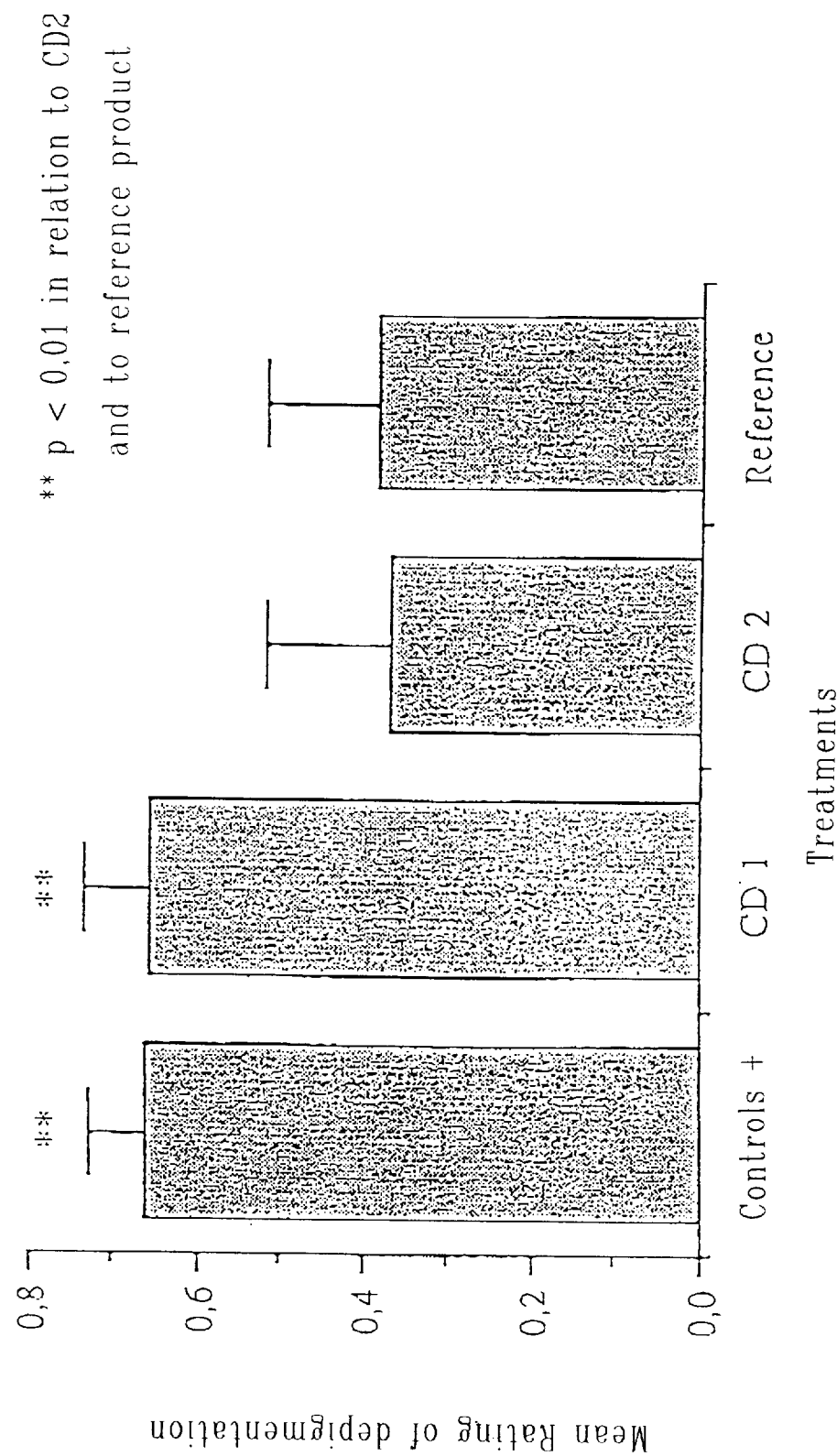
FIG. 3: comparative efficiency of various depigmenting treatments.

A comparison of the mean ratings of depigmentation (FIG. 3) shows a clearly higher efficacy (more than 70 to 80%) for cream CD1 and controls (+) in comparison with cream CD2 and with the reference product which has been tested at the same time. These results perfectly corroborate the macroscopical observations.

2.3 Local Tolerance

At the time of macroscopical examinations, not any intolerance symptoms have been registered all along the test.

However at histological examination, it has been noted in one mouse of the controls (+) group and in one mouse of the group CD1, a parakeratosis at the surface with accumulation of polynuclears. It has also be noted a significant hyperacanthosis with a parakeratosis in two animals treated with the reference product. One of these two animal moreover shown a deletion of the folds and the cutaneous rings.

3 Conclusions

The present study had as an objective to appreciate in the pigmented mice efficacy of two novel depigmenting creams referenced as CD1 and CD2, in comparison to a control (+) made of hydroquinone at 5% and to a reference cream taken up on the market.

From a macroscopical point of view, the cream CD1 evidenced the best depigmenting efficacy ahead controls (+), reference product and cream CD2. On the other part on the histological level, cream CD1 appeared to be as active as controls (+) and significatively better than cream CD2 and than the reference product.

In view of these results, it may be considered that cream CD1 is endowed with a depigmenting activity at least equivalent to that of controls (+) and in any case higher than the other tested formulation (CD2) and than the reference product. It has to be noted that tolerancy of cream CD1 is moreover noted as good since not any significant cutaneous damage has been proved after 12 weeks application.

EXAMPLE VI

Study in the Man

1—Selection Criteria

Inclusion criteria

Patients of 18 to 75 years old, which bear a chloasma, a senile lentigo, pigmentar marks located on the face or on other uncovered parts Exclusion criteria:
- congenital pigmented marks,
- concomitant sun exposition,
- under UV apparatus exposition,
- intake of photosensibilizing drugs, such as tetracycline or phenothiazines.

Methods of Treatment

Placebo CMP v. Cream CD1 with the same distribution (9 patients in each group), same package.

Two applications per day on the marks for to days. The rythm of examinations has been $D_0$, $D_{21}$, $D_{45}$ and $D_{60}$.

The criteria of evaluation have been based on clinical observations and advices from the patient, and on a medical monitoring with advice from the investigator.

Evaluation of the Efficiency

Controls by means of an analogic scale graduated as follows:

| Quotation at $D_0$ (basic condition) | Quotation at $D_{21}$, $D_{45}$, $D_{60}$ |
|---|---|
| 6 = +++++ = very strong pigmentation | 6 = no depigmentation |
| 5 = ++++= strong pigmentation | 5 = unclear depigmentation |
| 4 = +++= medium pigmentation | 4 = medium depigmentation |
| 3 = ++= weak pigmentation | 3 = good depigmentation |
| 2 = += very weak pigmentation | 2 = very good depigmentation |
| 1 = ± = pigmentation barely visible | 1 = excellent depigmentation |
| 0 = 0 = no pigmentation | 0 = excellent depigmentation without any visible mark |

Evaluation of the Tolerance

Monitoring by means of clinical observations histories on some phenomenas (irritations, red blotches, burnings, smartings, desquamation, allergies):
- 0=excellent tolerance
- 1=good tolerance
- 2=weak tolerance
- 3=bad tolerance Expression of the Results and Statistical Analysis The quotations registered for efficacy at each examination have been globally analysed by means of the non parametric Wilcoxon's test.

2—Results

Analysis of the Efficacy of the Treatment

The results put in figures of the intensity evaluation of the depigmentation are put in writing in the table herebelow. Examination of that shows that the depigmenting action displays in a clear manner at the end of 21 days of treatment. Then it is observed an increase of the depigmenting action until to the 45th day. It is from this time that the depigmenting effects appeared as the most significative in comparison with $J_0$ ($p \leq 0,01$)

TABLE 1

Evaluation of the depigmentation in patients treated with cream CD1

| Pathology | Patient n° | Days of treatment |||
|---|---|---|---|---|
| | | D0 | D21 | D45 |
| Dyschromia of the neck | 1 | 4 | 3 | 1 |
| Dyschromia of the face | 2 | 6 | 3 | 2 |
| Residual dyschromia of the legs | 3 | 5 | 4 | 3 |
| Chloasma of the pregnancy | 4 | 3 | 1 | — |
| Dyschromia of the face | 5 | 3 | 2 | 0 |
| Bilateral dyschromia of the feets | 6 | 4 | 3 | 1 |
| Generalized dyschromia of Addison's type | 7 | 4 | 2 | 1 |
| Dyschromia after-effects of an ophtalmic herpes zoster | 8 | 3 | 1 | — |
| Dyschromia secondary to pityriasis (Gilbert's pink pityriasis) | 9 | 3 | 1 | 0 |
| Median | | 4,0 | 2,0** | 1,0** |

Wilcoxon's test in relation to DO
*p ≤ 0,05
**p ≤ 0,01
***p ≤ 0,001

Generally speaking, the major part of the patients did not come anew at the last consultation (Day=60th day) since in every cases the initial lesions have almost disappeared from the 45th treatment day.

In the placebo group, all the patients have interrupted the treatment from the first days of treatment due to the total lack of efficacy. The great difference between the treated group and the placebo group has as a consequence to clear up the double blind due to the quasi-instantaneous knowledge of the group which received the active ingredient and the placebo group.

Analysis of the Local Tolerance

The thus obtained results on the tolerancy of the treatment, at the level of the area of application, have been in the whole excellent. The lack of irritation, redness, smartling, allergy, pain, burning and desquamation during the whole period of treatment, evidences the very good long-term tolerancy of cream Bruni clear®.

Legend of the Figures

FIG. 1

The asterisks indicate the statistically significant differences. Each plot corresponds to the average of individual quotations for 6 animals.

FIG. 2

The subdivisions inside each bar represent the proportion of cutaneous edges of different pigmentation.

FIG. 3

Each bar represent the average of individual values modified by the standard deviation for 6 animals.

What is claimed is:

1. A dermocosmetic composition containing as active ingredients, a combination endowed with depigmenting activity comprising:

a) an acid mixture comprising
  i) 20 to 30% by weight of glycolic acid,
  ii) 1 to 15% by weight of kojic acid, and
b) 20 to 35% by weight of an active component of plant extracts consisting essentially of

| | |
|---|---|
| aqueous/butylene glycol tannic acid extract of nutgall: | 2% by weight |
| Yukinoshita: | 1% by weight |
| Naringin extracted from grapefruit: | 0.75% by weight |
| butylene glycol extract of Sohakuhi: | 7.5% by weight |
| White mulberry: | 13% by weight |
| butylene glycol extract of Lemon: | 2.5% by weight | and the remaining part is a carrier suitable for the composition.

2. A composition of claim 1 wherein the plant extracts are obtained from the stems, the leaves and/or the roots of the plants.

3. A composition of claim 1 wherein the weight ratio between the acid mixture (a) and the active component of plant extracts (b) is between 50/50 and 70/30.

4. A composition of claim 1, further comprising ceramides.

5. A method of treating hyperpigmentation in humans comprising topically applying to the skin of humans in need thereof, a depigmenting effective amount of the composition of claim 1.

6. The method of claim 5 wherein the human's skin is that which shows an irregular pigmentation.

7. A method of treating hyperpigmentations in humans comprising topically administering to humans in need thereof a depigmenting effective amount of the composition of claim 2.

* * * * *